United States Patent [19]

Haneishi et al.

[11] Patent Number: 5,064,760
[45] Date of Patent: Nov. 12, 1991

[54] PROCESS FOR THE PRODUCTION OF AN IMIDAZOLEDIONE COMPOUND BY A STRAIN OF *STREPTOMYCES HYGROSCOPICUS*

[75] Inventors: Tatsuo Haneishi; Mutsuo Nakajima; Akio Torikata; Takao Okazaki, all of Tokyo; Manbu Tohjigamori; Katsuhiko Kawakubo, both of Shiga, all of Japan

[73] Assignee: Sankyo Company Limited, Tokyo, Japan

[21] Appl. No.: 537,510

[22] Filed: Jun. 13, 1990

Related U.S. Application Data

[63] Continuation-in-part of Ser. No. 227,433, Jul. 29, 1988, Pat. No. 4,952,234, which is a continuation-in-part of Ser. No. 825,861, Feb. 4, 1986, abandoned.

[30] Foreign Application Priority Data

Feb. 5, 1985 [JP] Japan ................................. 60-20603

[51] Int. Cl.⁵ .......................... C12P 17/16; C12P 1/06; C12N 1/20
[52] U.S. Cl. .................... 435/118; 435/169; 435/898
[58] Field of Search ........................ 435/118, 169, 898

[56] References Cited

U.S. PATENT DOCUMENTS

| | | | |
|---|---|---|---|
| 4,181,715 | 1/1980 | Kondo et al. | 435/898 |
| 4,273,571 | 6/1981 | Berg et al. | 435/169 |
| 4,320,135 | 3/1982 | Kathawala | 424/273 R |
| 4,415,669 | 11/1983 | Hernandez | 435/118 |

*Primary Examiner*—Douglas W. Robinson
*Assistant Examiner*—C. Geckle
*Attorney, Agent, or Firm*—Frishauf, Holtz, Goodman & Woodward

[57] ABSTRACT

A new compound, named Substance No. 51262, may be produced by cultivating a suitable microorganism of the genus Streptomyces, especially the new strain SANK 63584 (FERM BP-958). Said compound has herbicidal and growth retardant properties. Said compound has the following structural formula:

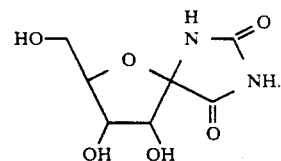

6 Claims, 3 Drawing Sheets

PROCESS FOR THE PRODUCTION OF AN IMIDAZOLEDIONE COMPOUND BY A STRAIN OF STREPTOMYCES HYGROSCOPICUS

BACKGROUND TO THE INVENTION

The present invention relates to a new compound which we have called "Substance No. 51262" and which has herbicidal activity and plant growth retardative activity. The invention also relates to herbicides and plant growth regulators containing this substance as the active ingredient and to a process for the preparation of this substance. Substance No. 51262 is produced by the cultivation of a microorganism of the genus *Streptomyces*.

BRIEF SUMMARY OF INVENTION

Figure 1:
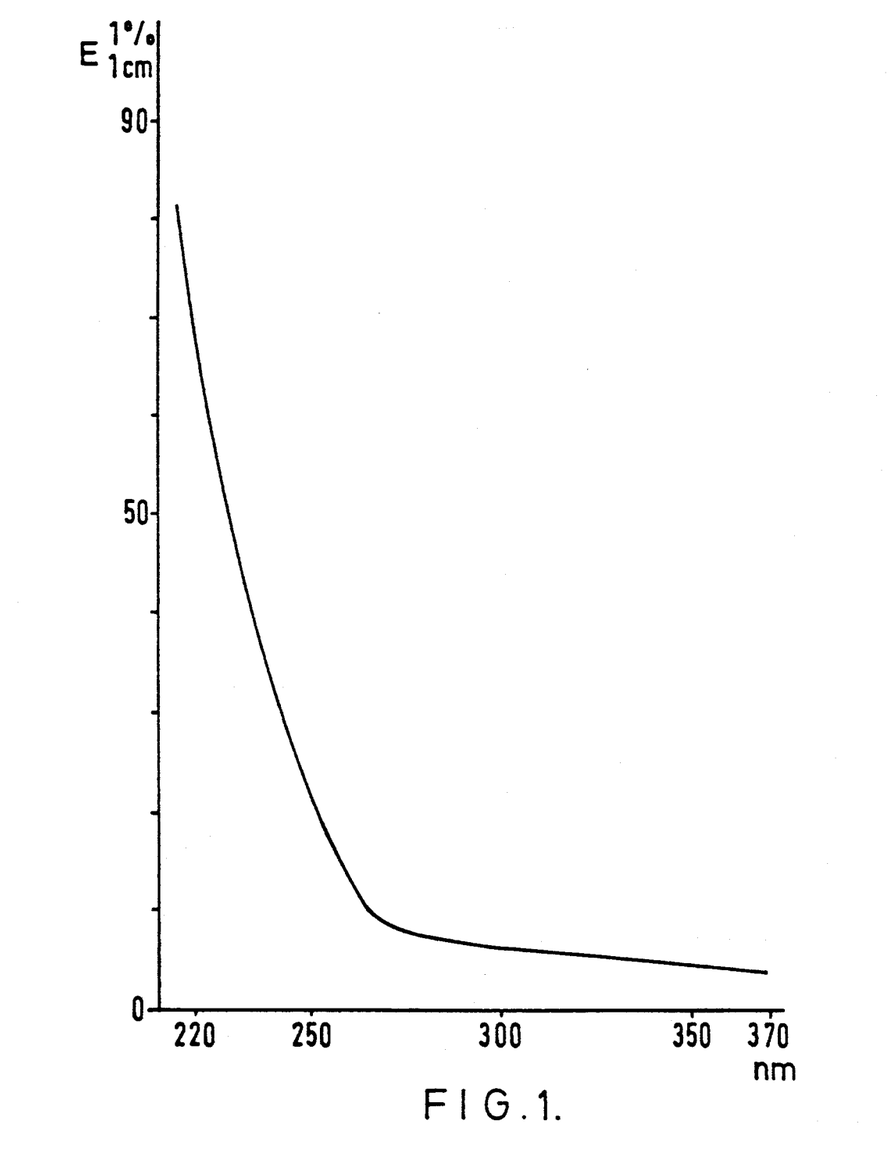
Figure 2:
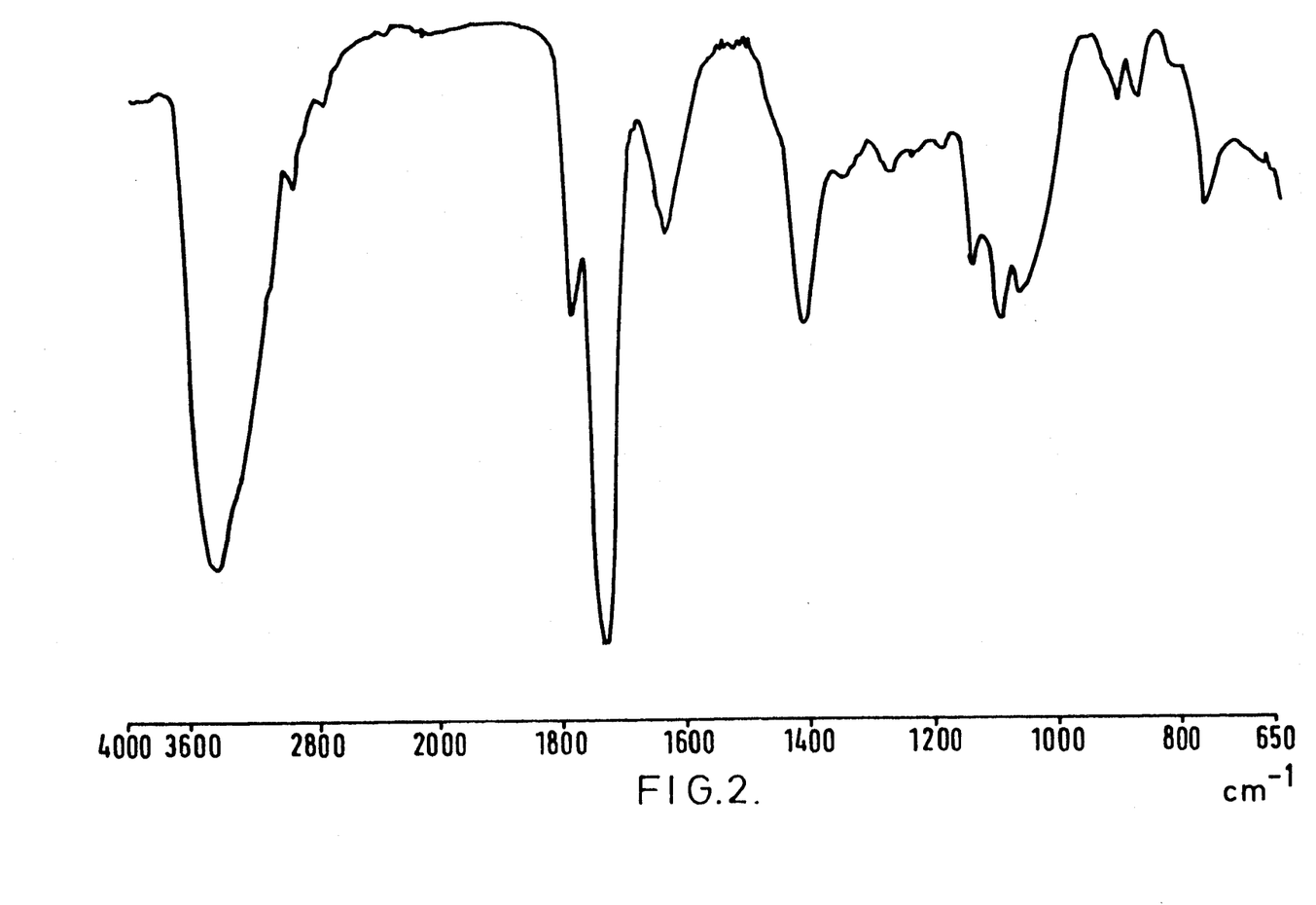
Figure 3:
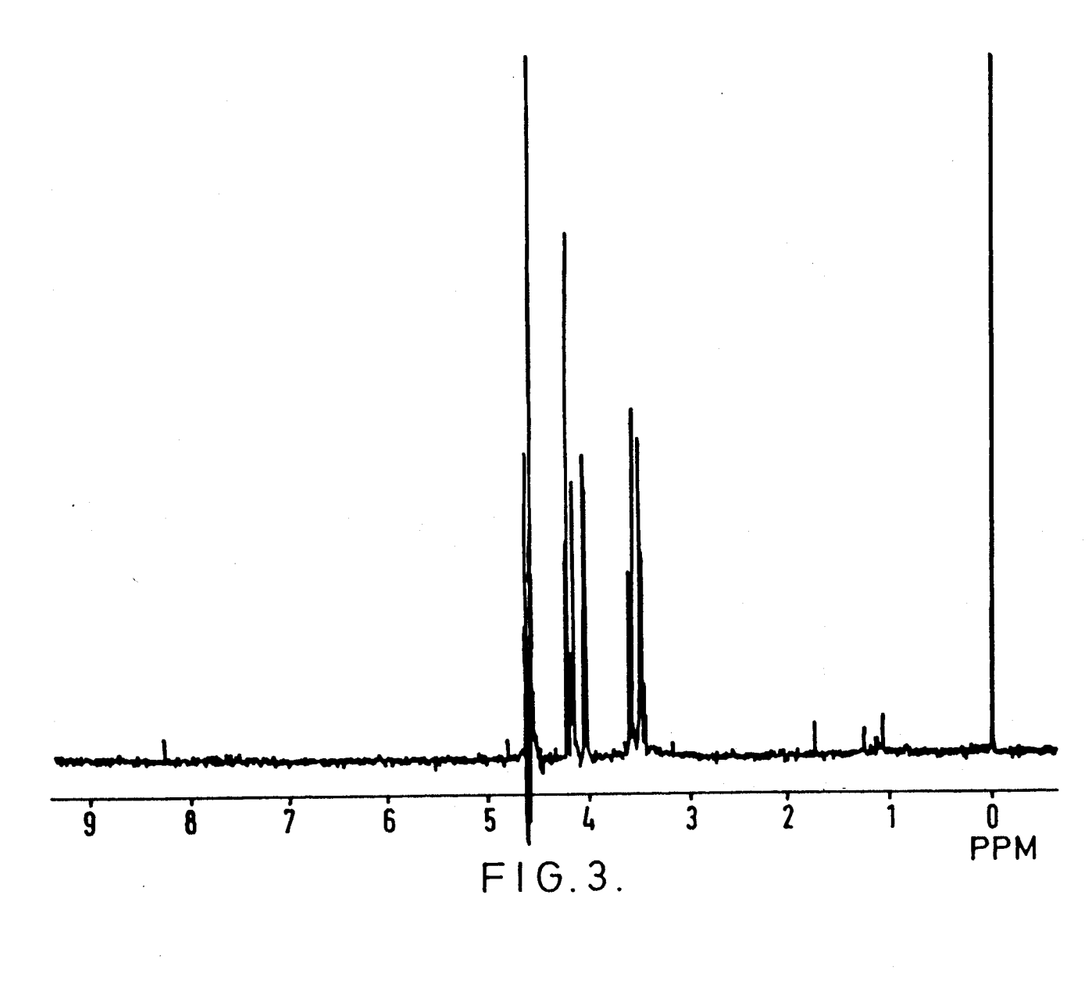

Substance No. 51262 may be characterized by its properties, as follows:

Substance No. 51262 is a compound represented by the following structural formula
- (a) appearance:
  neutral, colorless crystals;
- (b) specific rotation:
  $[\alpha]^{25} = +28.8°$ (C=1.04, $H_2O$, sodium D-line);
- (c) elemental analysis:
  Calculated for $C_7H_{10}N_2O_6$:
  C. 38.54%; H. 4.62%; N. 12.84%;
  Found: C. 38.55%; H. 4.53%; N. 12.90%;
- (d) melting point of crystals:
  187°–189° C.;
- (e) molecular formula:
  $C_7H_{10}N_2O_6$;
- (f) molecular weight:
  218;
- (g) ultraviolet absorption spectrum:
  as shown in FIG. 1 of the accompanying drawings, it exhibits no absorption maxima above 220 nm in aqueous solution;
- (h) infrared absorption spectrum:
  the infrared absorption spectrum, as measured in a KBr disc, is as shown in FIG. 2 of the accompanying drawings;
- (i) nuclear magnetic resonance spectrum:
  the nuclear magnetic resonance spectrum ($\delta$ ppm) as measured at 400 MHz in heavy water, using tetramethylsilane as the external standard, is as shown in FIG. 3 of the accompanying drawings;
- (j) solubility:
  soluble in water, methanol and ethanol;
  insoluble in ethyl acetate and acetone;
- (k) color reactions:
  positive for sulfuric acid, anisaldehyde/sulfuric acid and potassium permanganate reactions;
- (1) thin layer chromatography:
  Rf value=0.3; on a silica gel plate No. 5715 (Merck Co.) developed with a 50:10:2 by volume mixture of ethyl acetate, isopropanol and water.

The invention also provides an agrochemical composition for herbicidal or plant growth regulatory activity comprising Substance No. 51262 as the active ingredient.

The invention still further provides a process for preparing Substance No. 51262 by cultivating a Substance No. 51262-producing microorganism of the genus *Streptomyces* and separating Substance No. 51262 from the cultured broth.

Detailed Description of Invention

Substance No. 51262 is produced by the cultivation of a microorganism of the genus Streptomyces and preferably a microorganism of the species represented by the newly discovered Streptomyces strain herein identified as Streptomyces sp. SANK 63584.

The newly discovered microorganism, Streptomyces sp. SANK 63584, has the characteristics described hereafter. These characteristics were determined by cultivation on Various media prescribed by the ISP (International Streptomyces Project) or with the media recommended by S. A. Waksman in Volume 2 of "The Actinomycetes", in all cases at a temperature of 28° C.

1. Morphological Characteristics

Vegetative hyphae of strain SANK 63584 grow well, with branching, on the media prescribed by the ISP after cultivation at 28° C. for 14 days. The aerial hyphae show simple branches under microscopic examination. The shape of the spore chain is mainly a close spiral. The surface structure of the spore chain is warty-rugose. No special organs, such as sclerotia, fragmented vegetative hyphae or sporangia, were observed.

2. Culture Characteristics

The aerial mycelium became moist and black as cultivation proceeded. No soluble pigment was produced. Table 1 shows the results obtained after cultivation for 14 days at 28° C. on various standard culture media. The color names and numbers used were assigned according to the "Guide to Color Standard", a Manual published by Nippon Shikisai Kenkyusho, Tokyo, Japan.

TABLE 1

| Culture medium | Item | Behavior of strain SANK 63584 |
|---|---|---|
| Sucrose-nitrate agar | G | Less good, flat, pale yellowish orange (2-9-9) |
| | AM | Slightly formed, velvety, brownish white (1-6-6) |
| | R | Pale brown (2-8-9) |
| | SP | None |
| Glucose-asparagine agar | G | Good, flat, pale yellowish orange (2-9-9) |
| | AM | Slightly formed, velvety, white |
| | R | Pale yellowish orange (2-9-9) |
| | SP | None |
| Glycerol-asparagine agar (ISP5) | G | Abundant, flat, pale yellowish orange (2-9-9) |
| | AM | Less good, velvety, white |
| | R | Pale yellowish orange (2-9-9) |
| | SP | None |
| Inorganic salts-starch agar (ISP4) | G | Abundant, flat, pale yellowish brown (6-7-9) |
| | AM | Abundantly formed, velvety, brownish gray (1-5-6) |
| | R | Yellowish brown (6-6-8) |
| | SP | None |
| Tyrosine agar (ISP7) | G | Abundant, flat, pale yellowish brown (4-8-9) |
| | AM | Less good, velvety, white |
| | R | Yellowish brown (6-7-8) |
| | SP | None |
| Peptone-yeast extract-iron agar (ISP6) | G | Abundant, flat, pale Yellowish brown (4-8-9) |
| | AM | Slightly formed, velvety, white |
| | R | Pale yellowish brown (6-7-9) |
| | SP | None |
| Nutrient agar (Difco) | G | Good, flat, pale yellowish brown (4-8-9) |
| | AM | Slightly formed, velvety, white |
| | R | Pale yellowish brown (4-8-9) |
| | SP | None |
| Yeast extract-malt extract agar | G | Abundant, flat, pale yellowish brown (6-7-9) |

TABLE 1-continued

| Culture medium | Item | Behavior of strain SANK 63584 |
|---|---|---|
| (ISP2) | AM | Abundantly formed, velvety, brownish gray (1-5-6) |
| | R | Yellowish brown (6-5-8) |
| | SP | None |
| Oatmeal agar (ISP3) | G | Abundant, flat, pale yellowish brown (6-7-9) |
| | AM | Abundantly formed, velvety, brownish white (1-6-6) |
| | R | Yellowish brown (6-6-8) |
| | SP | None |
| Water agar | G | Poor, flat, pale yellowish orange (2-9-9) |
| | AM | Less good, velvety, light brownish white (1-7-6) |
| | R | Light brownish gray (2-8-7) |
| | SP | None |
| Potato extract-carrot extract agar | G | Poor, flat, pale yellowish orange (2-9-9) |
| | AM | Less good, velvety, brownish gray (1-5-6) |
| | R | Light brownish white (1-7-6) |
| | SP | None |

The abbreviations under the heading "Item" have the following meanings:
G:Growth; AM:Aerial Mycelium;
R:Reverse side; SP:Soluble pigments.

3. Physiological Properties

The physiological properties of strain SANK 63584 are shown in Table 2.

TABLE 2

| | |
|---|---|
| Hydrolysis of starch | + |
| Liquefaction of gelatin | + |
| Reduction of nitrate | + |
| Coagulation of milk | − |
| Peptonization of milk | + |
| Range of growth temperature (Medium 1) | 11–46° C. |
| Optimum temperature of growth (Medium 1) | 24–38° C. |
| Growth in NaCl (Medium 1) | Growth in 7% No growth in 10% |
| Decomposition of casein | + |
| Decomposition of tyrosine | + |
| Decomposition of xanthine | − |
| Production of melanoid pigment (Medium 2) | − |
| Production of melanoid pigment (Medium 3) | − |
| Production of melanoid pigment (Medium 4) | − |

The media referred to above are as follows:
Medium 1: Yeast extract—malt extract agar (ISP 2);
Medium 2: Tryptone-yeast extract broth (ISP 1);
Medium 3: Peptone-yeast extract iron agar (ISP 6);
Medium 4: Tyrosine agar (ISP 7).

The utilization of carbon sources after incubation of strain SANK 63584 for 14 days was examined using a Pridham-Gottlieb basal agar medium. Since strain SANK 63584 can grow, at least to some extent, in this basal medium without any added carbon source, it is difficult to describe exactly its ability to utilize carbon sources. The relative utilizations are shown in Table 3, taking the utilization of the above basal medium as negative (−) as a control.

TABLE 3

| D-Glucose | + | D-Fructose | + |
|---|---|---|---|
| L-Arabinose | ± | L-Rhamnose | − |
| D-Xylose | ± | Sucrose | − |
| Inositol | − | Raffinose | − |

TABLE 3-continued

| D-Mannitol | + | Control | − |
|---|---|---|---|

+ : Utilized
± : Slightly utilized
− : Not utilized

4. Whole Cell Components

The cell walls of strain SANK 63584 were examined using the method of Becker et al. [Applied Microbiology, 12, 421 (1964)]. L.L-diaminopimelic acid and glycine were detected and hence it was concluded that the cell walls were of Type 1. The whole cell sugar components of strain SANK 63584 were investigated by the method of Lechevalier [Journal of Laboratory and Clinical Medicine, 71, 934 (1968)]. No characteristic sugar pattern was recognized.

From the above findings, the new strain was confirmed to belong to the genus Streptomyces, of the Actinomycetes, and was named Streptomyces sp. SANK 63584. It has recently been assigned to the species Streptomyces hygroscopicus and may thus also be called Streptomyces hygroscopicus SANK 63584.

Identification of strain SANK 63584 was carried out according to the ISP Reports, Bergey's Manual of Determinative Bacteriology (8th edition). "The Actinomycetes", volume 2 and other recent literature concerning the taxonomy of the streptomycetes.

The strain SANK 63584 has been deposited with the Fermentation Research Institute, Agency of Industrial Science and Technology, Ministry of International Trade and Industry, Japan, on 14th December 1984 under the Accession No. FERM P-8004 and was redeposited in accordance with the conditions stipulated by the Budapest Treaty with said Fermentation Research Institute on 9th January 1986 under the Accession No. FERM BP-958.

It has been established that strain SANK 63584 produces Substance No. 51262. However, as is well known, the properties of microorganisms falling within the general category of the actinomycetes can vary considerably and such microorganisms can readily undergo mutation, both through natural causes and as the result of induction by artificial means. Accordingly, the process of the present invention embraces the use of any microorganism which ca be classified within the genus Streptomyces and which shares with the new strain SANK 63584 the characteristic ability to produce Substance No. 51262.

The cultivation of microorganisms of the genus Streptomyces, and particularly strains of the species Streptomyces hydroscopicus, in accordance with the present invention to produce Substance No. 51262 can be performed under conditions conventionally employed for the cultivation of actinomycetes species preferably in a liquid culture, and desirably with shaking or stirring and aeration. The nutrient medium used for the cultivation is completely conventional and contains such constituents as are commonly used in the cultivation of the actinomycetes. Specifically, the medium should preferably contain an assimilable carbon source, suitable examples of which include glucose, maltose, sucrose, mannitol, molasses, glycerol, dextrin, starch, soybean oil and cottonseed oil; an assimilable nitrogen source, suitable examples of which include soybean meal, peanut meal, cottonseed meal, Fermamine, fish meal, corn steep liquor, peptone, meat extract, pressed yeast, yeast extract, sodium nitrate, ammonium nitrate or ammonium sulfate; and one or more inorganic salts, such as sodium chloride, phosphates, calcium carbonate and, if required, trace metal salts. Where cultivation is effected in a liquid medium, it is generally desirable to incorporate an anti-foaming agent (for example silicone oil, vegetable oil or a suitable surfactant) in the medium.

The cultivation is suitably performed at a substantially neutral pH value and at a temperature of from 24° to 38° C. more preferably from 24° to 30° C. most preferably at about 28° C.

The production of Substance No. 51262 as cultivation proceeds may be monitored by a variety of conventional techniques for monitoring the production of biologically active substances by microbial culture and which require little or no elaboration here. A suitable technique is to assess the inhibitory activity of the cultured broth against a sensitive plant species. e.g. *Brassica Rapa* (L) var. "Komatsuna".

The amount of Substance No. 51262 produced normally reaches a maximum after cultivation has proceeded for 60 to 120 hours and it is clearly desirable to separate the Substance No. 51262 from the culture medium no later than the time when this maximum has been reached. However, this period may vary, depending upon the cultivation conditions and techniques, and a shorter or longer period may be appropriate, depending upon the circumstances. The correct cultivation time may readily be assessed for every case by routine experiment, using suitable monitoring techniques, e.g. as described above.

Substance No. 51262 is soluble in water and is mainly released into the liquid portion of the cultured broth and can thus be recovered by removing solid matter, including the mycelium, for example by filtration, preferably using a filter aid such as diatomaceous earth, or by centrifugation. It can then be recovered from the separated liquid portion by conventional techniques making use of its specific physicochemical properties and, if desired, then purified.

Substance No. 51262 is preferably separated from other products in said liquid portion by means of an adsorbent, either by adsorbing the impurities or by adsorbing the Substance No. 51262 or by adsorbing both separately or together and then eluting the Substance No. 51262. A wide range of adsorbents may be used; examples which we have found to be particularly satisfactory include: activated carbon; and resinous adsorbents such as Amberlite (registered trade mark) XAD-2, XAD-4 or XAD-7 (Products of Rohm and Haas) and Diaion (registered trade mark) HP10, HP20, CHP20P or HP50 (Products of Mitsubishi Chemical Industries Co., Ltd.). The impurities present in the liquid portion may be removed by passing the solution containing Substance No. 51262 through a layer or column of one or more of the aforementioned adsorbents or by adsorbing Substance No. 51262 on one or more of the adsorbents and then eluting the Substance No. 51262 with a suitable eluent. Suitable eluents include mixtures of methanol, acetone or butanol with water.

The Substance No. 51262 thus obtained may be further purified by various means. Suitable methods include partition column chromatography using a cellulose product, such as Avicel (a registered trade mark for a product of Asahi Chemical Industry Co., Ltd.) or Sephadex LH-20 (a registered trade mark for a product of Farmacia, Sweden). The impurities present in the liquid portion containing the Substance No. 51262 may also be removed by adsorbing them on various kinds of cation-exchange resins (strong or weak), such as Dowex 50W (a registered trade mark for a product of Dow Chemical Co., Ltd) or Amberlite IRC-50 (a registered trade mark for a product of Rohm and Haas), or on an anion-exchange resin (such as Dowex 1 or Diaion WA10).

Further purification of Substance No. 51262 may be effected by chromatography using silica gel, if required. A single one or any combination of these purification techniques may be used in order to obtain pure Substance No. 51262 having the physicochemical properties described above.

Examination of the literature has not revealed any known compound whose properties coincide exactly with these and accordingly it has been concluded that Substance No. 51262 is a new compound.

Substance No. 51262 shows both herbicidal and growth retarding activity for plants. A herbicidal activity means that the substance harms plants and may finally kill them. On the other hand, a retarding activity means that the substance retards or suppresses plant growth without showing such herbicidal activity as to result in necrosis or death of the plants. The response of a plant to the substance (i.e. whether a herbicidal or growth retarding effect is experienced) will vary depending upon the method of application, the concentration of Substance No. 51262 and the sensitivity of the treated plant to the substance. As is demonstrated subsequently, the compound of the invention has an excellent herbicidal activity against various weeds, when applied both pre- and post-emergence, and is therefore useful as a herbicide for application to foliage. We also demonstrate hereafter that the substance can retard plant growth without killing the plants. Accordingly, it is expected to be useful to prevent rice plants from falling over by shortening the rice plant culms, to decrease the time or frequency of mowing, pruning or trimming by retarding the growth of grass and garden plants, to dwarf flowering plants and so on.

The agrochemical composition of the present invention, whether for use as a herbicide or plant growth regulator, may comprise the Substance No. 51262 alone or this Substance in admixture with a carrier and/or adjuvant. The composition may be made into any form conventional in the agrochemical field, for example it may be formulated as a dust, coarse dust, granules microgranules, wettable powder, water-soluble powder or liquid formulation. It is, of course, not necessary to use a completely pure form of Substance No. 51262 in the composition and, of course, purification can be suspended at any stage and the resulting crude substance may be used as the active ingredient of the composition.

The carriers used in such a composition may be a synthetic or natural, organic or inorganic substance and are mixed with the compound of the invention in order to make the storage, transportation and handling of the active ingredient easier o to assist translocation of the active ingredient into the plants. Carriers may be solid or liquid. Examples of solid carriers include such inorganic substances as: clay, talc, diatomite, kaolin, bentonite, calcium carbonate, gypsum, synthetic precipitated silica, attapulgite, zeolite or pumice; such synthetic and natural resins as coumarone resin, alkyd resins, polyvinyl chloride, ester gum or xanthan gum; such waxes as carnauba wax or paraffin wax; and other organic materials, such as nut shells (e.g. of walnuts or other nuts) or soybean powder. Examples of liquid carriers include water and alcohols, such as methanol, ethanol, isopropanol or ethylene glycol.

Where the composition is to include a surfactant, this may be ionic or non-ionic and is used to assist dispersion, wetting or spreading of the composition. Examples of anionic surfactants include sodium and calcium salts of ligninsulfonic acid, sodium oleate, sodium dodecyl benzenesulfonate, sodium dialkyl sulfosuccinates, sodium, ammonium and amine salts of polyoxyethylene alkyl aryl ether sulfates or of polyoxyethylene alkyl ether sulfates or the free acids or salts of polyoxyethylene alkyl aryl ether phosphates or of polyoxyethylene alkyl phosphates. Examples of cationic surfactants include the higher aliphatic amines and ethylene oxide condensates with such amines, quaternary ammonium chlorides, N-alkylamine acetates and N-alkylamine oxides. Amphoteric surfactants include betaines and amino acid-type surfactants. Examples of non-ionic surfactants include: glyceride and sucrose esters of fatty acids, ethylene oxide condensates with higher aliphatic alcohols, ethylene oxide condensates with alkylphenols or alkylnaphthols, amides or ethoxylated amides of higher fatty acids, higher fatty acid esters of sorbitan or of ethoxylated sorbitans, higher fatty acid esters of glycerol borates or of ethoxylated glycerol borates and copolymers of ethylene oxide with propylene oxide.

The compositions of the present invention may, if desired, also contain other components, for example: protective colloidal agents, such as gelatine, gum arabic, casein, polyvinyl alcohol or carboxymethyl cellulose, or thickeners, such as sodium polyphosphate or bentonite. For wider applicability and labour saving, the composition of the invention can, if desired, be combined with other fungicides, insecticides, herbicides, plant growth regulators and fertilizers.

The invention is further illustrated by the following Examples, of which Examples 1 and 2 illustrate the preparation of Substance No. 51262, whilst Examples 3 to 7 illustrate the effect of Substance No. 51262 and Examples No. 8 to 13 illustrate compositions containing it. Examples 14 describes the determination of the structural formulae of Substance No. 51262.

EXAMPLE 1

Preparation of Substance No. 51262

One loopful growth of Streptomyces sp. strain SANK 63584 was inoculated into each of four 500 ml Erlenmeyer flasks, each containing 80 ml of a medium having the following composition (percentages are by weight):

| | |
|---|---|
| Glucose | 3% |
| Yeast | 1% |
| Soybean meal | 3% |
| Calcium carbonate | 0.4% |
| $MgSO_4.7H_2O$ | 0.2% |
| Antifoaming agent (Nissan Disfoam CB-442, available from Nissan Chemical Industries Limited) | 0.01% |
| Water to | 100% |
| pH 7.2, before sterilization. | |

The microorganism was then cultured using a rotary shaker at 220 rpm for 72 hours at a temperature of 28° C.

2 ml of the resulting seed culture were inoculated into each of 130 500 ml Erlenmeyer flasks, each containing 80 ml of the same culture medium, and the microorganism was cultured using a rotary shaker at 220 rpm, at a temperature of 28° C. for 96 hours. The resulting cultured broths and washings, totalling 11.4 liters, were combined and 1 kg of a Celite 545 (trademark for a product of Johns Manville Products Corp.) filter aid was added and the mixture was filtered to give 11 liters of a filtrate having a pH value of 7.1. The filtrate was then passed through a chromatography column packed with 3 liters of activated carbon (a product of Wako Pure Chemicals Industries Limited) to adsorb the Substance No. 51262.

The column was washed with 4.5 liters of deionized water and then the desired substance was eluted with 15 liters of 10% v/v aqueous acetone. The 15 liters of active eluate were condensed by evaporation under reduced pressure and then lyophilized to give 61 g of a crude powder containing the desired Substance No. 51262. If desired, this crude powder could be used as such for agrochemical use.

The crude powder was then adsorbed on a chromatography column containing 500 ml of Avicel (a trademark for a product of Asahi Chemical Industry Co Ltd) which had previously been equilibrated with acetonitrile. The column was then eluted, in turn, with 2 liters of acetonitrile, with 3 liters of 97% v/v aqueous acetonitrile and finally with 6 liters of 85% v/v acetonitrile. The eluate was collected in fractions of 1 liter each, and the desired Substance No. 51262 was found to be present in the 6th to 9th fractions. These fractions were pooled, condensed by evaporation under reduced pressure and then lyophilized to give 4.6 g of powder. The powder was dissolved in a small amount of 50% v/v aqueous methanol and adsorbed onto a Sephadex LH-20 (a trademark for a product of Farmacia, Sweden) column, which had previously been equilibrated with 50% v/v aqueous methanol. The column was eluted using 50% v/v aqueous methanol and the eluate was collected in fractions of 15 ml. Fractions No. 36–50 contained the desired Substance No. 51262 and were collected, pooled, condensed by evaporation under reduced pressure and passed again through the same Sephadex LH-20 column. The eluted fractions were collected and lyophilized, giving 334 mg of a sample of Substance No. 51262, of purity about 70%.

300 mg of this sample were adsorbed on a silica gel column (a product of Merck Co.) which had previously been equilibrated with a 10:1 by volume mixture of chloroform and methanol. The desired substance was eluted with a 6:1 by volume mixture of chloroform and methanol and the eluate was collected in fractions of 15 ml. Fractions No. 22–60 were collected, pooled, condensed by evaporation under reduced pressure and then subjected to silica gel preparative thin layer chromatography, using a 50:10:2 by volume mixture of ethyl acetate, isopropanol and water as the developing solvent. The desired substance was extracted with a 6:1 by volume mixture of chloroform and methanol, and the extract was condensed by evaporation under reduced pressure and then lyophilized, to give 25.5 mg of Substance No. 51262 as a colorless powder having the following properties:

(a') appearance:
neutral, colorless powder;
(b') specific rotation:
$[\alpha]^{20} = +24.4°$ (C=0.61 $H_2O$, sodium D-line):
(c') elemental analysis:
Calculated for $C_7H_{10}N_2O_6.H_2O$:
C. 35.59%; H. 5.08%: N. 11.86%;

Found C. 35.65%; H. 5.00%; N. 11.71%;
and properties (e)–(1) as heretofore described.

EXAMPLE 2

Preparation of Substance No. 51262

260 mg of partially purified Substance No. 51262 were prepared by the procedure described in Example 1 (essentially identical up to the stage where the crude sample of purify about 70% was prepared) and this partially purified compound was dissolved in a small amount of water. The solution was adsorbed onto a column containing 300 ml of Diaion CHP-20P and eluted with water. The eluate was collected in fractions of 5 ml and the desired Substance No. 51262 was eluted in fractions No. 61–67, showing a single spot on thin layer chromatography. These fractions were pooled, condensed by evaporation under reduced pressure and lyophilized, to give 41 mg of the desired Substance No. 51262 as a colorless powder having the same properties as the product of Example 1.

EXAMPLE 3

Preparation of Crystalline Substance No. 51262

The procedure described in Example 2 was repeated to give 130 mg of Substance No. 51262 as a colorless powder. The whole of this powder was dissolved in hot acetone, and the resulting solution was then cooled. The crystals which separated were collected, to give 37 mg of Substance No. 51262 as colorless needles having the properties (a)–(1) heretofore described.

EXAMPLE 4

Inhibitory Effect on the Germination of Komatsuna Seeds

Sterilized cotton was placed on the bottom of a test tube (10 mm×100 mm) to a height of about 5 mm, and the cotton was then soaked with 0.5 ml of either distilled water or of an aqueous solution containing various concentrations of Substance No. 51262. About 10 seeds of the plant Komatsuna [Brassica Rapa (L) var. Komatsuna Hara] were placed into each test tube and allowed to stand at 28° C. for 3 days to determine the inhibitory concentration of Substance No. 51262, assessed by the presence or absence of germination. The minimum inhibitory concentration of Substance No. 51262 against the germination of Komatsuna seeds was thus determined to be 3.13 μg/ml.

EXAMPLE 5

Pre-emergence Soil Treatment Test

A plastic pot was filled with upland soil, giving a surface area of soil of about 150 cm$^2$, and then seeds from the following annual upland weeds were sowed onto the soil, and then covered with the same soil: *Setaria faberi* Herrm.; *Digitaria sanouinalis* (L) Scorp; *Echinochloa crus-galli* (L.) Beauv.; *Setaria viridis* (L.) Beauv.; *Amaranthus retroflexus* L.; *Brassica arvensis* (L.) Kuntze; *Chenopodium album* L.; *Ambrosia artemisiifolia* L.; *Abutilon theophrasti* Medic; and *Sida spinose* L.

One day after sowing the seeds, an aqueous solution of Substance No. 51262 (prepared as described in Example 13) was sprayed uniformly over the soil in an amount of 15 ml per pot. The pots were then allowed to stand in a greenhouse for 3 weeks, after which the growth of the weeds was observed. The herbicidal effect of Substance No. 51262 was assessed by comparing the growth of treated weeds with those of a control which had not been treated and the results are reported in the following Table 4, using the following codes:

| Growth inhibition | 0–5% | efficacy | 0 |
| --- | --- | --- | --- |
| Growth inhibition | 6–30% | efficacy | 1 |
| Growth inhibition | 31–50% | efficacy | 2 |
| Growth inhibition | 51–70% | efficacy | 3 |
| Growth inhibition | 71–95% | efficacy | 4 |
| Growth inhibition | 96–100% | efficacy | 5 |

TABLE 3

| | Dosage (active ingredient kg/ha) | |
| --- | --- | --- |
| | 2.5 | 1.25 |
| Narrowleaved weeds | | |
| *Setaria faberi* Herrm. | 5 | 5 |
| *Digitaria sanquinalis* (L) Scop. | 5 | 5 |
| *Echinochloa crus-galli* (L) Beauv. | 5 | 5 |
| *Setaria viridis* (L) Beauv. | 5 | 5 |
| Broadleaved weeds | | |
| *Amaranthus retroflexus* L. | 5 | 4 |
| *Brassica arvensis* (L) Kuntze | 5 | 5 |
| *Chenopodium album* L. | 3 | 1 |
| *Abutilon theophrasti* Medic. | 5 | 3 |
| *Sida spinose* L. | 5 | 4 |
| *Ambrosia artemisiifolia* L. | 5 | 2 |

EXAMPLE 6

Foliage Treatment

Seeds of weeds (as listed in Table 5) were sowed in pots, covered with soil and allowed to stand in a greenhouse, following the procedure described in Example 5. 10 days after sowing, an aqueous solution of Substance No. 51262 (prepared following the procedure described hereafter in Example 11) having the concentration shown in Table 5 was mixed with 0.03% w/w of a Gramin S (a trademark of Sankyo Co Ltd) spreader. 5 ml of the resulting solution were sprayed into each pot. The weeds were observed 10 days after treatment and the herbicidal effect of Substance No. 51262 was determined and reported, using the codes described in Example 5.

TABLE 3

| | Dosage (active ingredient ppm) | |
| --- | --- | --- |
| | 500 | 250 |
| Narrowleaved weeds | | |
| *Setaria faberi* Herrm. | 4 | 3 |
| *Digitaria sanquinalis* (L) Scop. | 5 | 5 |
| *Echinochloa crus-galli* (L) Beauv. | 5 | 5 |
| *Setaria viridis* (L) Beauv. | 5 | 5 |
| Broadleaved weeds | | |
| *Amaranthus retroflexus* L. | 5 | 3 |
| *Brassica arvensis* (L) Kuntze | 5 | 5 |
| *Chenopodium album* L. | 3 | 2 |
| *Abutilon theophrasti* Medic. | 5 | 5 |
| *Sida spinosa* L. | 5 | 5 |
| *Ambrosa artemisiifolia* L. | 5 | 5 |

EXAMPLE 7

Plant Growth Retardation

A plastic pot was filled with upland soil to provide a surface area of soil of 150 cm$^2$. Seeds of paddy field rice, soybeans, corn and cotton were sowed. Tubers of the perennial weed, purple nutsedge (*Cyperus rotundus*) were then planted into each pot and the seeds and tubers were covered with the same soil. The pots were placed in a greenhouse for 10 days, after which aqueous solutions of Substance No. 51262 (prepared as described hereafter in Example 11) to the required concentrations were mixed with 0.03% v/v of the spreader Gramin S. 5 ml of the resulting solution were sprayed onto each pot. The growth of the resulting plants were compared after 2 weeks with a control which had not been so treated. Those plants treated with 125 ppm of Substance No. 51262 showed a growth retardation of about 50% for all plants, whilst those pots treated with 500 ppm of Substance No. 51262 showed almost complete growth inhibition of the shoot and rhizome of the purple nutsedge.

EXAMPLE 8

Toxicity

A solution of Substance No. 51262 was administered intravenously to mice in an amount of 100 mg/kg bodyweight. The mice were observed for 14 days and no abnormalities were detected.

EXAMPLE 9

Granules

After cultivation following the procedure described in Example 1, the culture broth was adsorbed onto an active carbon column. The active fraction eluted with 10% v/v aqueous acetone was evaporated to dryness under reduced pressure, to give a crude powder. This crude powder was dissolved in water, to give a 50% w/w aqueous solution and this was adsorbed onto granular pumice (size 10–48 mesh, Tyler standard) to give granules.

EXAMPLE 10

Wettable Powder 50 parts by weight of the crude powder described in Example 9, 3 parts of sodium dodecyl benzenesulfonate, 2 parts of polyvinyl alcohol and 45 parts of clay were uniformly mixed and pulverized to give a wettable powder.

EXAMPLE 11

Water-soluble Powder 50 parts of Substance No. 51262, 2 parts of polyoxyethylene nonylphenyl ether, 10 parts of synthetic silica and 38 parts of ammonium sulfate were mixed uniformly to give a water-soluble powder.

EXAMPLE 12

Liquid Formulation 10 parts of Substance No. 51262 and 2 parts of sodium lauryl sulfate were dissolved uniformly in 88 parts of methanol, to give a liquid formulation.

EXAMPLE 13

Liquid Formulation 10 parts of Substance No. 51262 and 2 parts of sodium dodecyl benzenesulfonate were dissolved in 88 parts of water, to give a liquid formulation.

EXAMPLE 14

Determination of the Structure of Substance No. 51262

The elucidation of the plane structure and its relative configuration was made as set out below:

(1) Determination of molecular formula

The $QM^+$ was determined to be m/e 219 by the positive ion FAB mass spectroscopic measurement, while the $QM^-$ was determined to be m/e 217 by the negative ion FAB mass spectroscopic measurement.

Therefore, the molecular weight was determined to be 218.

Further, a high resolution mass spectroscopic measurement revealed that $QM^+219$ was assigned to $C_7H_{11}N_2O_6$ (obs., 219.06175; calcd., 219.06175; number of unsaturation, 3.5), giving the molecular formula $C_7H_{10}N_2O_6$ (number of unsaturation, 4).

(2) Presence and number of exchangeable hydrogen atoms

Two methyl groups were introduced to Substance No. 51262 when it was treated with diazomethane. Five trimethylsilyl groups were introduced to Substance No. 51262 when it was treated with trimethylsilyl chloride in pyridine. Four acetyl groups were introduced to Substance No. 51262 when it was treated with acetic anhydride in pyridine, and a further methyl group was introduced by a further treatment with diazomethane.

From these results, it was estimated that Substance No. 51262 had five exchangeable or active hydrogen atoms, of which one was an acidic hydrogen atom resistant to acetylation.

(3) Estimation of the structure

The mass spectrum of the penta(trimethylsilyl) derivative of Substance No. 51262 showed the same group of peaks at m/e 319. 230, 217 and 103 as those of tetra(trimethylsilyl)derivative or uridine (FIG. 1), suggesting the presence of a sugar moiety, such as furanose, in Substance No. 51262.

FIG. 1

On the assumption that Substance No. 51262 has the furanose moiety, two formulae (A) and (B), each having three active hydrogen atoms in the furanose moiety, may be given.

(A)

-continued (B)

Then, since Substance No. 51262 is assumed to have five active hydrogen atoms, x of (A) of Y of (B) are assumed to have two remaining active hydrogen atoms, respectively. Thus, the possibility of the formula (A) having only one hydrogen atom in X is likely negated, while the formula (B) having two hydrogen atoms in Y meets the estimation. Since one of the two hydrogen atoms in Y is of high degree of acidity and since the number of unsaturation of Substance No. 51262 is four, a plane formula (C) in which furanose and hydantoin forms a spiro ring was tentatively given. For the dimethyl derivative of Substance No. 51262 obtained by the reaction with diazomethane, a plane formula (D) was tentatively given.

(C)

(D)

(4) Demonstration of the plane formula (C)

The MS/MS spectrum (collisionally activated dissociation spectrum) was measured at QM+219 by positive ion FAB mass spectrometry. The molecular ion peak observed was supported by the fragment peaks shown in FIG. 2.

FIG. 2

That the sugar moiety of Substance No. 51262 is furanose was demonstrated from the coupling patterns (chemical shifts and coupling constants, see Table 1 below) of $H_2$, $H_3$, $H_4$, $H_5$ and $H_{5'}$, in (C) by the $^1$H-NMR measurement of $CD_3OD$ and $d_6$—DMSO. The hydroxy protons were observed at 5.60, 4.68 and 4.78 (δ pmm) in $d_6$—DMSO and these peaks were assigned to 2-$OH_a$, 3-$OH_b$ and 5-$OH_c$ in (C), respectively, by way of the decoupling method. The NH protons were observed at 8.5 and 10.9 (δ ppm) of $NH_d$ and $NH_e$, respectively.

The infrared absorption peaks at 1780 amd 1720 cm$^{-1}$ (KBr) supported the presence of the carbonyl groups of the hydantoin moiety.

Thus, the plane structure of Substance No. 51262 was demonstrated to be (C), judging from the findings described above.

TABLE 1

| H | $^1$H-NMR Spectrum Data of (C) and (D) | | |
|---|---|---|---|
| | (C: $CD_3OD$) | (C: $d_6$-DMSO) | (D: $CD_3OD$) |
| $H_2$ | 4.24 | 4.11 | 4.46 |
| | (d, $J_{23}$ = 6.0) | (t, $J_{23}$ = 5.9, $J_{2a}$ = 5.1) | (d, $J_{23}$ = 5.9) |
| $H_3$ | 4.04 | 3.87 | 4.08 |
| | (dd, $J_{34}$ = 2.2) | (ddd, $J_{34}$ = 2.2, $J_{3b}$ = 10.2) | (dd, $J_{34}$ = 1.5) |
| $H_4$ | 4.22 | 4.03 | 4.27 |
| | (dt, $J_{45}$ = 4.2) | (dt, $J_{45}$ = 5.0) | (dt, $J_{34}$ = 3.6) |
| $H_5$ | 3.62 (m)*2 | 3.41 (m)*2 | 3.67 (m)*2 |
| $H_{5'}$ | | | |
| 2-$OH_a$ | — | 5.60 (d) | — |
| 3-$OH_b$ | — | 10.2 (d) | — |
| 5-$OH_c$ | — | 4.78 (t) | — |
| $NH_{(d)}$ | — | 8.5 (s)*1 | — |
| $NH_{(e)}$ | — | 10.9 (br.s)*1 | — |
| N—$CH_{3(f)}$ | — | — | 2.93 (s) |
| N—$CH_{3(g)}$ | — | — | 2.97 (s) |

*1 exchangeable with $D_2O$
*2 at the center of the multiplet

(5) Determination of the relative configuration

The spatial structure of Substance No. 51262 was determined from the NOE difference spectrum by the measurement of $^1$H-NMR.

The NOE (Nuclear Overhauser Effect) was observed at $H_3$ and $H_2$ by irradiation at $H_5$ and at $H_{5'}$. This shows that the furanose moiety is of the ribose form. The NOE was observed at $CH_{3(f)}$ by irradiation at $H_2$ of the N-methyl derivative (D). Likewise, the NOE was observed at $H_2$ by the irradiation at $CH_{3(f)}$ of the N-methyl derivative (D). Thus, the N-methyl derivative (D) must have the conformational formula (E) in which $CH_{3(f)}$ is on the same side as $H_2$ in respect of the ribose ring.

It was therefore concluded that the relative configuration of Substance No. 51262 is as shown in formula (F).

(E)

(F)

We claim:

1. A process for preparing a compound of the formula which comprises cultivating *Streptomyces hygroscopicus* SANK 63584 (FERM BP-958) under conditions effective to produce a recoverable amount of said compound and recrevicing said compound from the culture medium.

2. The process as claimed in claim 16, wherein said culturing is effected at a temperature of from 24° to 38° C.

3. The process as claimed in claim 16, wherein said culturing is effected at a temperature of about 28° C.

4. The process of claim 16 wherein said compound has the formula

5. The process as claimed in claim 4, wherein said culturing is effected at a temperature of from 24° to 38° C.

6. The process as claimed in claim 4, wherein said culturing is effected at a temperature of about 28° C.

* * * * *

UNITED STATES PATENT AND TRADEMARK OFFICE
CERTIFICATE OF CORRECTION

PATENT NO. : 5,064,760

DATED : November 12, 1991

INVENTOR(S) : HANEISHI et al

It is certified that error appears in the above-identified patent and that said Letters Patent is hereby corrected as shown below:

Title Page -

- Section [75] Inventors :

Replace the name of the fifth inventor "Manbu TOHJIGAMORI" with --Man_a_bu TOHJIGAMORI--.

- Section [63] Related U.S. Application Data:

Replace "Continuation-in-part" at the beginning of the sentence with --This application is a divisional application--.

Column 1, line 17, after "BRIEF SUMMARY OF INVENTION", insert the following

-- Substance No.51262 is a compound represented by the following structural formula:

UNITED STATES PATENT AND TRADEMARK OFFICE
CERTIFICATE OF CORRECTION

PATENT NO. : 5,064,760
DATED : November 12, 1991
INVENTOR(S) : HANEISHI et al

It is certified that error appears in the above-identified patent and that said Letters Patent is hereby corrected as shown below:

The stereo configuration of the Substance 51262 is depicted by the following formula:

--.

Column 1, lines 21-22, delete "Substance 51262...structural formula".

Column 1, line 56, replace "(1) thin layer..." with --(1) thin layer...--.

Column 4, line 46, replace "ca" with --can--.

Column 4, line 55, after "species", insert --,--.

Column 7, line 41, replace "Examples 14" with --Example 14--.

Column 9, line 2, replace "(1)" with --(1)--.

Column 9, line 30, replace "(1)" with --(1)--.

UNITED STATES PATENT AND TRADEMARK OFFICE
CERTIFICATE OF CORRECTION

PATENT NO. : 5,064,760

DATED : November 12, 1991

INVENTOR(S) : HANEISHI et al

It is certified that error appears in the above-identified patent and that said Letters Patent is hereby corrected as shown below:

Column 9, line 56, replace "sanouinalis" with
   --sanquinalis--.

Column 12, line 40, replace the present Fig.1 with the following:

Fig. 1

Column 13, line 11, replace "x" with --X--.

Column 13, line 57, to the right of the structural
   formula, insert --(D)--.

Column 14, line 22, replace "and $H_5$" with --and $H_{5'}$--.

Column 14, line 29, replace "amd" with --and--.

UNITED STATES PATENT AND TRADEMARK OFFICE
CERTIFICATE OF CORRECTION

PATENT NO. : 5,064,760

DATED : November 12, 1991

INVENTOR(S) : HANEISHI et al

It is certified that error appears in the above-identified patent and that said Letters Patent is hereby corrected as shown below:

Column 15, replace formulas (E) and (F) with the following:

(E)

(F)

Column 16, line 9 (Claim 1), replace "cultivating" with --culturing--.

Column 16, line 12 (Claim 1), replace "recrevicing" with --recovering--.

UNITED STATES PATENT AND TRADEMARK OFFICE
CERTIFICATE OF CORRECTION

PATENT NO. : 5,064,760

DATED : November 12, 1991

INVENTOR(S) : HANEISHI et al

It is certified that error appears in the above-identified patent and that said Letters Patent is hereby corrected as shown below:

Column 16, line 14 (Claim 2), replace "claim 16" with
--claim 1--.

Column 16, line 17 (Claim 3), replace "claim 16" with
--claim 1--.

Column 16, line 19 (Claim 4), replace "claim 16" with
--claim 1--.

Column 16, lines 21-28 (Claim 4), replace formula with
the following:

UNITED STATES PATENT AND TRADEMARK OFFICE
CERTIFICATE OF CORRECTION

PATENT NO. : 5,064,760

DATED : November 12, 1991

INVENTOR(S) : HANEISHI et al

It is certified that error appears in the above-identified patent and that said Letters Patent is hereby corrected as shown below:

Column 16, line 31 (Claim 5), replace "from24°" with
--from 24°--.

Signed and Sealed this

Fifth Day of April, 1994

Attest:

BRUCE LEHMAN

Attesting Officer

Commissioner of Patents and Trademarks